(12) United States Patent
Zhang et al.

(10) Patent No.: US 11,903,401 B2
(45) Date of Patent: Feb. 20, 2024

(54) METHOD FOR INCREASING YIELD OF AMADORI REARRANGEMENT PRODUCTS BASED ON INHIBITION MECHANISM OF TEA POLYPHENOLS AND DEOXYOSONES TO DEGRADATION OF AMADORI REARRANGEMENT PRODUCTS

(71) Applicants: Jiangnan University, Wuxi (CN); Anhui Qiangwang Flavouring Food Co., Ltd., Jieshou (CN)

(72) Inventors: Xiaoming Zhang, Wuxi (CN); Junhe Yu, Wuxi (CN); Heping Cui, Wuxi (CN); Huan Zhan, Wuxi (CN); Yun Zhai, Wuxi (CN); Jingyang Yu, Wuxi (CN); Shuqin Xia, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 594 days.

(21) Appl. No.: 17/055,130

(22) PCT Filed: Apr. 21, 2020

(86) PCT No.: PCT/CN2020/085780
§ 371 (c)(1),
(2) Date: Nov. 13, 2020

(87) PCT Pub. No.: WO2021/073064
PCT Pub. Date: Apr. 22, 2021

(65) Prior Publication Data
US 2021/0368830 A1    Dec. 2, 2021

(30) Foreign Application Priority Data
Oct. 18, 2019   (CN) .......................... 201910994751.2

(51) Int. Cl.
| | | |
|---|---|---|
| *A23L 3/3562* | (2006.01) | |
| *A23L 29/30* | (2016.01) | |
| *C07H 1/00* | (2006.01) | |
| *A23L 27/21* | (2016.01) | |

(52) U.S. Cl.
CPC .......... *A23L 3/3562* (2013.01); *A23L 27/215* (2016.08); *A23L 29/30* (2016.08); *C07H 1/00* (2013.01)

(58) Field of Classification Search
CPC ....... C07H 1/00; A23L 27/215; A23L 3/3562; A23L 29/30
See application file for complete search history.

(56) References Cited

U.S. PATENT DOCUMENTS

| | | |
|---|---|---|
| 2005/0031771 A1 | 2/2005 | Peterson |
| 2012/0288533 A1 | 11/2012 | Livney |

FOREIGN PATENT DOCUMENTS

| | | |
|---|---|---|
| CN | 104178357 A | 12/2014 |
| CN | 104273521 A | 1/2015 |
| CN | 105639651 A | 6/2016 |
| CN | 106749431 A | 5/2017 |
| CN | 106820253 A | 6/2017 |
| CN | 106905207 A | 6/2017 |
| CN | 110710668 A | 1/2020 |
| KR | 20150119991 A | 10/2015 |

OTHER PUBLICATIONS

Cui et al., "Synergistic Effect of a Thermal Reaction and Vacuum Dehydration on Improving Xylose-Phenylalanine Conversion to N-(1-Deoxy-D-xylulos-1-yl)-phenylalanine during an Aqueous Maillard Reaction", Sep. 2018, Journal of Agricultural and Food Chemistry, vol. 66, pp. 10077-10085 (Year: 2018).*
Kokkinidou, S., "Inhibition of Maillard Reaction Pathways and Off-flavor Development in UHT milk: Structure Reactivity of Phenolic Compounds", Jan. 2013, Proquest, LLC, UMI No. 3556097 (Year: 2013).*
Junhe Yu et al., Interaction of (−)-Epigallocatechin Gallate and Deoxyosones Blocking the Subsequent Maillard Reaction and Improving the Yield of N-(1-Deoxy-D-xylulos-1-yl)alanine, Journal of Agricultural and Food Chemistry, 2020, pp. 1714-1724, 68.
Xiaohong Yu et al., Effective Mechanism of (−)-Epigallocatechin Gallate Indicating the Critical Formation Conditions of Amadori Compound during an Aqueous Maillard Reaction, Journal of Agricultural and Food Chemistry, 2019, pp. 3412-3422, 67.

* cited by examiner

*Primary Examiner* — Jeffrey P Mornhinweg
*Assistant Examiner* — Kelly P Kershaw
(74) *Attorney, Agent, or Firm* — Bayramoglu Law Offices LLC

(57) ABSTRACT

A method for increasing the yield of Amadori rearrangement products (ARP) based on a mechanism in which addition of tea polyphenols to deoxyosones inhibits degradation of the ARP. The method includes the following steps: dissolving and mixing amino acid, sugar and tea polyphenol in water, and adjusting a pH value; placing the obtained mixed solution in a reaction flask, and heating the mixed solution at a constant temperature in a water bath to obtain a reaction solution; and performing vacuum decompression dehydration reaction at a constant temperature; after the reaction is completed, using an ice bath to terminate the reaction to obtain a solid reactant, and redissolving the solid reactant in water to obtain an ARP solution. This method promotes the formation of ARP and inhibits degradation of ARP, so that ARP is accumulated and enriched in a large amount (80% and above yield).

8 Claims, 18 Drawing Sheets

METHOD FOR INCREASING YIELD OF AMADORI REARRANGEMENT PRODUCTS BASED ON INHIBITION MECHANISM OF TEA POLYPHENOLS AND DEOXYOSONES TO DEGRADATION OF AMADORI REARRANGEMENT PRODUCTS

CROSS REFERENCE TO THE RELATED APPLICATIONS

This application is the national phase entry of International Application No. PCT/CN2020/085780, filed on Apr. 21, 2020, which is based upon and claims priority to Chinese Patent Application No. 201910994751.2, filed on Oct. 18, 2019, the entire contents of which are incorporated herein by reference.

TECHNICAL FIELD

The present invention relates to the fields of food chemistry and food additives, and in particular relates to a method for increasing the yield of Amadori rearrangement products based on a mechanism that addition of tea polyphenols to deoxyosones inhibits degradation of the Amadori rearrangement products.

BACKGROUND

An Amadori rearrangement product (ARP), as an important intermediate product in the early Maillard reaction process, has been widely studied. The ARP is formed by the following process: an aldose carbonyl group and an amino group undergo an addition reaction and lose a molecule of water to form Schiff base, the Schiff base is then cyclized to form a corresponding N-substituted aldose amine, and then the N-substituted aldose amine is converted into reactive 1-amino-1-deoxy-2-ketose by Amadori rearrangement. ARP plays an important role in the formation of flavor and color during food processing or storage. At present, the commonly used ingredients of salty condiments in China are advanced Maillard reaction products (MRPs). Although the flavor is strong, most of the MRP are highly volatile. Especially under high-temperature processing conditions such as cooking and baking, it is difficult to maintain a stable aroma-enhancing effect, the problems of aroma loss and non-lasting aroma are prominent, and application thereof is greatly restricted. However, ARP has relatively stable physical and chemical properties at room temperature and retains relatively high reactivity under heating conditions. ARP can readily undergo a subsequent Maillard reaction and produce volatile flavor substances. Therefore, ARP can be used as an "active flavor precursor". By preparing such suitable flavor precursors, an ideal sensory attribute during food processing can be formed in a controlled manner.

However, the yield of the active flavor precursor in a water phase usually does not exceed 5%, making it different to realize the commercialized production of the flavor precursor. At present, there have been certain studies on how to increase the ARP yield, for example, the ARP yield can be increased by synthesis in organic solvents such as absolute methanol. Such chemical methods have high physiological toxicity, pollute the environment, and have high production costs, so the methods are only suitable for theoretical research and cannot meet the needs of large-scale production. In addition, the use of sodium sulfite also has the effect of increasing the yield of ARP, but such chemical additives leave sulfite in the food. Recent studies have shown that sulfite can damage chromosomes and DNA, cause an increase in the rates of sister chromatid exchange (SCE) and micronucleus (MN) in human blood lymphocytes, and delay the mitotic cycle of lymphocytes and decrease the cell division index, and these effects have a significant dose-effect relationship. Therefore, the addition of sulfite not only has the risk of excessive intake, but also has great food safety problems. As people resist and reject the addition of chemical substances in food and urgently need natural healthy food, it is of great significance to study how to increase the yield of ARP and break through the technical barriers of low yield in water phase by adopting a natural, green, and new technical method without potential toxic and side effects of synthetic compounds, thereby realizing large-scale industrial production of the ARP as an active flavor precursor.

SUMMARY

In view of the shortcomings of the prior art, the present invention provides a method for increasing the yield of Amadori rearrangement products based on a mechanism that addition of tea polyphenols to deoxyosones inhibits degradation of the Amadori rearrangement products. The present invention has simple operation, mild conditions, and high yield of prepared products.

The technical solution of the present invention is as follows:

The method for increasing the yield of Amadori rearrangement products based on the mechanism that addition of tea polyphenols to deoxyosones inhibits degradation of the Amadori rearrangement products includes the following steps:

(1) taking and dissolving amino acid, sugar and tea polyphenol by adding water, and adjusting a pH value of the mixed solution;

(2) placing the mixed solution obtained in step (1) in a reaction flask, and heating at a constant temperature in a water bath to obtain a reaction solution; and (3) performing vacuum decompression dehydration reaction on the reaction solution obtained in step (2) at a constant temperature; after the reaction is completed, using an ice bath to terminate the reaction to obtain a solid reactant; and redissolving the solid reactant with water to obtain an ARP solution.

The tea polyphenol in step (1) includes at least one of epicatechin (EC), epigallocatechin (EGC), epicatechin gallate (ECG), epigallocatechin gallate (EGCG), catechin (C), gallocatechin (GC), catechin gallate (CG) and gallocatechin gallate (GCG).

The amino acid in step (1) is one or more of alanine, phenylalanine, serine and methionine.

The sugar in step (1) is one or more of ribose, xylose, arabinose and glucose.

Dosages of the amino acid, sugar and tea polyphenol in step (1) is: 10 parts of amino acid, 5-50 parts of sugar, 0.1-5 parts of tea polyphenol, and 200-1200 parts of water, calculated by mass parts.

In step (1), the pH value of the mixed solution is 6-9.

In step (2), the constant temperature of the water bath is 60-90° C., and the heating time is 30-100 mm.

In step (3), the constant reaction temperature is 60-90° C., and the reaction time is 5-60 min; and an ice bath condition is: the temperature of the ice bath is maintained at 0° C.

In step (3), the ARP yield in the ARP solution can reach 80% or above.

The beneficial technical effects of the present invention are:

(1) The mechanism that addition of tea polyphenols in a Maillard reaction increases the ARP yield in the present invention is mainly due to synergy of the following three aspects:

(a) Mechanism of inhibition of ARP degradation by tea polyphenols

Active sites C6 and C8 on an A ring of catechin compounds, main components of tea polyphenols, can trap the primary degradation product of ARP, namely deoxyosones, and a low-reactivity phenol-sugar adduct is formed, thereby blocking a downstream reaction path of ARP and inhibiting the degradation of ARP. FIGS. 14A-F show the total ion chromatograms after tea polyphenol EGCG is added in a sugar/amino acid system for thermal reaction. It can be seen that tea polyphenols and deoxyosones DP can form a di-adduct di-DP-EGCG (FIG. 14A) and a monoadduct mono-DP-EGCG (FIG. 14D/14E), thereby blocking the downstream Maillard reaction path and inhibiting the degradation of ARP. The trap mechanism is shown in FIG. 15, and is an important basis for increasing the yield of ARP.

(b) Promotion of conversion of ARP precursor Schiff base to ARP by vacuum decompression dehydration The vacuum decompression dehydration process can increase the conversion rate of ARP by promoting the formation of an ARP precursor, Schiff base. As shown in FIG. 11, in a system without the addition of tea polyphenol EGCG, the yield of ARP obtained by vacuum decompression dehydration is 42.1%. Compared with the ARP yield of 2.2% in an atmospheric water phase, the yield is increased by 19 times, which proves that the vacuum decompression dehydration process can promote the formation of ARP.

(c) Synergistic effect of tea polyphenols and vacuum decompression dehydration

After tea polyphenols are added, the vacuum decompression dehydration process promotes the conversion of the ARP precursor Schiff base to ARP, and the addition of tea polyphenols inhibits the degradation of ARP, so that ARP is accumulated and enriched within a very short period of time. Such a synergistic effect significantly increases the ARP conversion rate. As shown in FIG. 1, the ARP yield can be increased to 94.8%, which is increased by 225.2% compared to the ARP yield of 42.1% obtained by vacuum decompression (FIG. 11). A kinetic model of ARP formation in the process is shown in FIG. 16. Route A is kinetic parameters of ARP in the vacuum decompression dehydration process when no tea polyphenols are added, and route B is kinetic parameters of ARP in the vacuum decompression dehydration process after tea polyphenols are added. At the same time, compared with the system without tea polyphenols addition, the activation energy of ARP formation $Ea_2$=70.88 kJ/mol>$Ea_2'$=60.35 kJ/mol, which may be because that the tea polyphenols and ARP form unstable intermediates of ARP-catechins (FIG. 15), and further the activation energy of conversion of sugar/amino acid to ARP is reduced, such as the ARP adduct ARP-EGCG detected in FIG. 14B/14C. Therefore, according to the principle of catalytic kinetics, tea polyphenols catalyze the formation of ARP to a certain extent. Through kinetic simulation, the calculation shows that the ARP generation rate $k_2'>k_2$, and the degradation rate $k_4'<k_4$, which proves that the addition of tea polyphenols promotes the formation of ARP and inhibits degradation of ARP.

(2) In the prior art, due to the low yield of ARP in a water phase, ARP is mostly prepared and synthesized in an organic phase. The technical method has physiological toxicity, environmental pollution and complicated operation, cannot obtain food-grade products, and is not suitable for industrial production. The method of the present invention for increasing the yield of ARP by using tea polyphenols has the advantages of food-grade synthesis, simple operation, greenness, no pollution, low cost, and easy industrial production. The ARP obtained by the technology can be directly applied to food ingredients or seasoning products.

(3) The tea polyphenols used in the present invention are natural food additives with strong anti-oxidation capacity extracted from tea, and have antibacterial effects and strong physiological activities, including resisting cancer, resisting mutation, and scavenging free radicals from the body. In the application process, tea polyphenols show characteristics of strong anti-oxidation capacity, no peculiar smell, and no potential toxic and side effects of synthetic compounds, and are of great significance for the development of functional semi-finished food seasonings (active flavor precursor ARP). Therefore, the present invention utilizes the technology of using tea polyphenols to promote the formation of ARP and inhibit degradation of ARP, so as to not only significantly increase the yield of ARP, but also increase the functional activity and shelf life of foods using ARP.

(4) The technology of using tea polyphenols to increase the yield of ARP in a water phase of the present invention not only overcomes the obstacle of low yield of ARP in the water phase, but also selects the natural additives tea polyphenols which are naturally available as raw materials. Compared with processing additives used in an organic phase method and a group protection method, the method greatly reduces the accounting cost, safety cost and environmental cost of production.

(5) The preparation process adopted by the present invention is simple in operation, and simple in equipment; the reaction is carried out at mild temperature; the preparation time is short and the yield is high. The process technology meets the green, scientific and sustainable industrial design concept, and has high edible safety. Therefore, the technology can be directly applied to actual production and has high practical application value.

BRIEF DESCRIPTION OF THE DRAWINGS

FIG. 14F shows the total ion chromatogram of an adduct of tea polyphenol EGCG. FIGS. 14B-14C show the total ion chromatograms of an adduct of ARP (an adduct of ARP-EGCG). FIG. 14A shows the total ion chromatogram of degradation product DP such as di-adduct di-DP-EGCG. FIGS. 14D-14E show the total ion chromatograms of degradation products DP such as monoadduct mono-DP-EGCG.

DETAILED DESCRIPTION OF THE EMBODIMENTS

The present invention will be described in detail below with reference to the drawings and embodiments.

Embodiment 1

(1) 8.90 kg of alanine, 32.00 kg of xylose and 0.5 kg of EGCG were taken and dissolved by adding 500 kg of water, and a pH value of the mixed solution was adjusted to 7.5.

(2) The mixed solution was placed in a thermal reaction flask under normal pressure, and heated at a temperature of 90° C. in a water bath for 60 min to obtain a reaction solution.

(3) The reaction solution obtained in step (2) was transferred into a flask and subjected to a vacuum decompression dehydration reaction at a constant temperature of 90° C. for 10 min. Then, an ice bath was used to terminate the reaction to obtain a solid reactant, and the solid reactant was redissolved with water to obtain an ARP solution.

Figure 1:
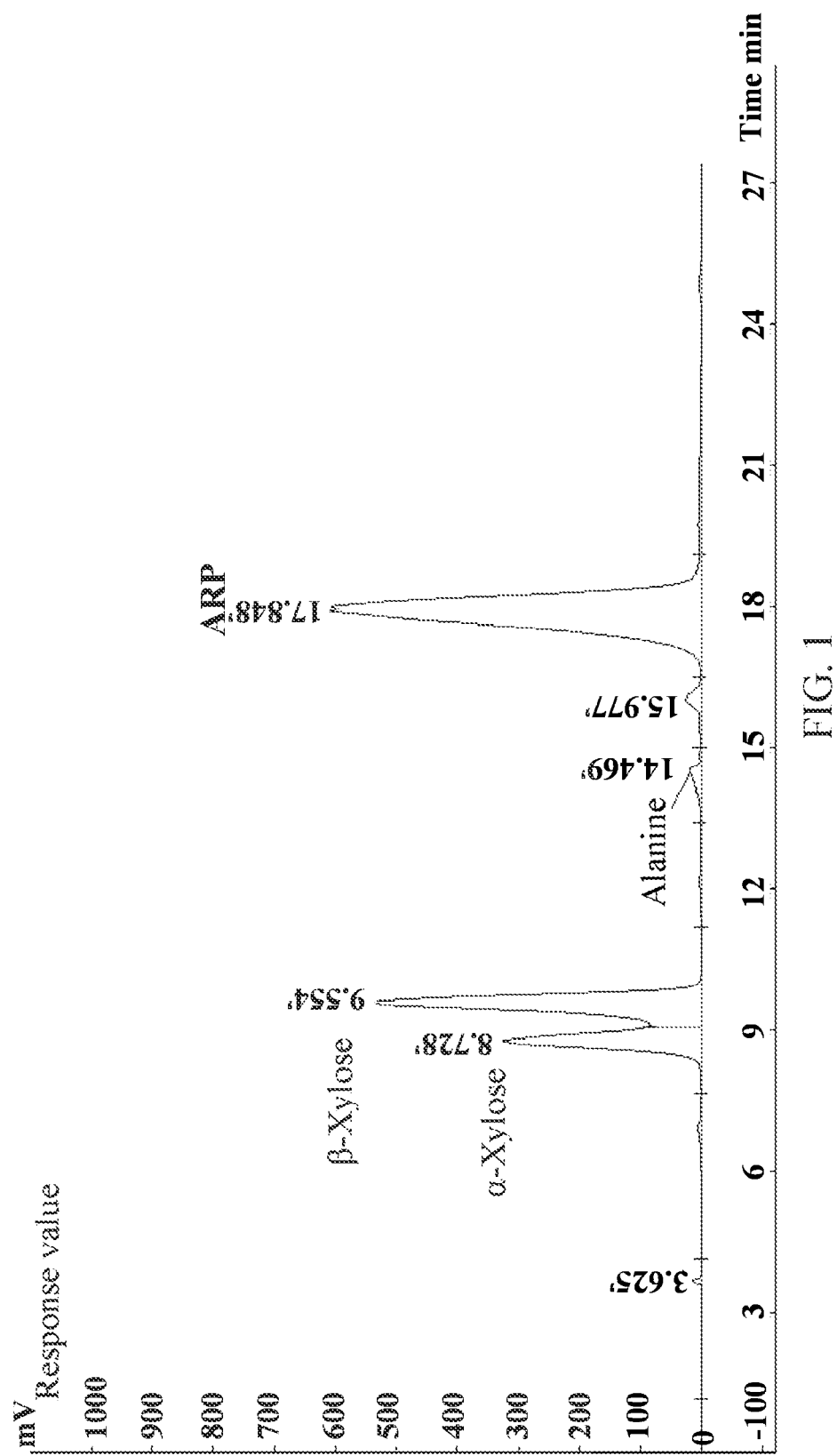
FIG. 1 is a chromatogram of an ARP solution prepared by an alanine/xylose reaction in a water phase system added with EGCG in Embodiment 1.
Figure 2A:
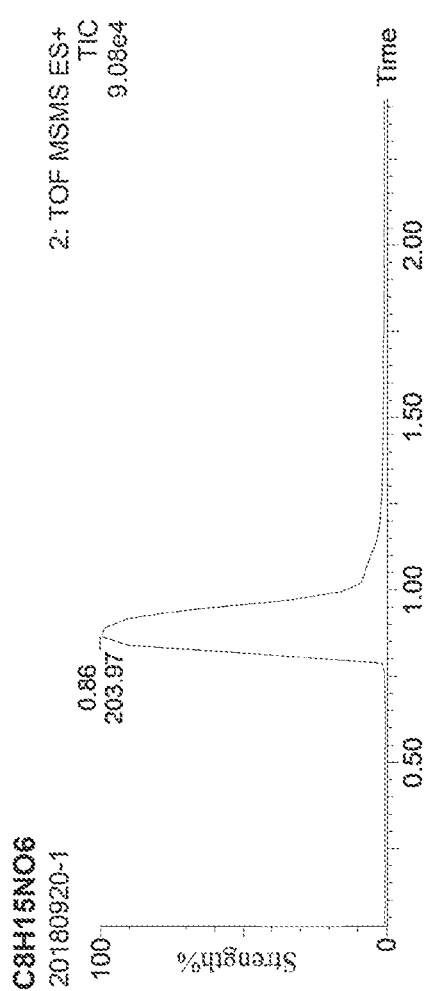
FIG. 2A shows a total ion chromatogram of ARP prepared by a purified alanine/xylose reaction and qualitatively obtained by LC/MS/MS in Embodiment 1.
Figure 3:
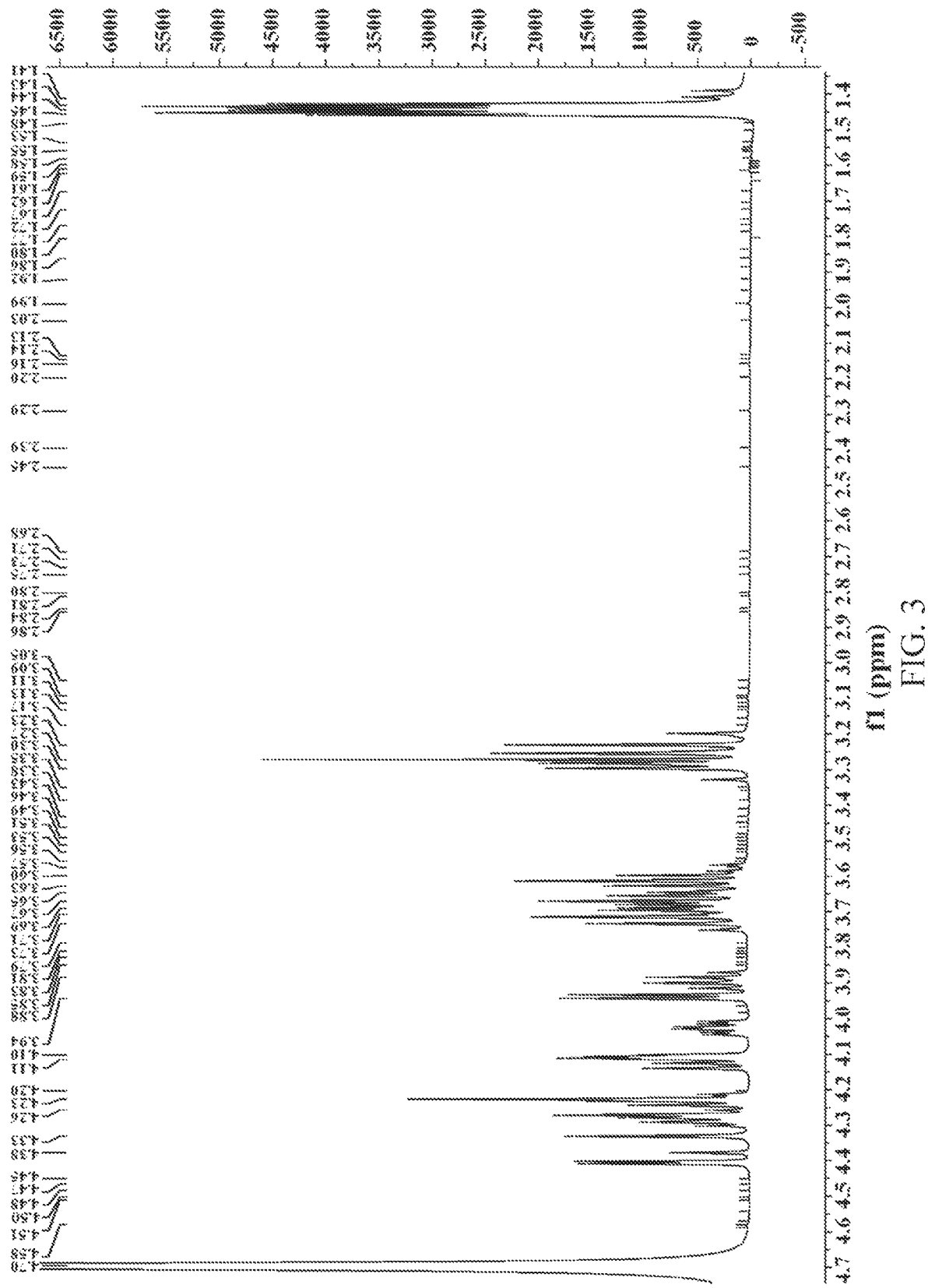
FIG. 3 is a hydrogen nuclear magnetic resonance spectrum of ARP prepared by an alanine/xylose reaction in Embodiment 1.
Figure 4:
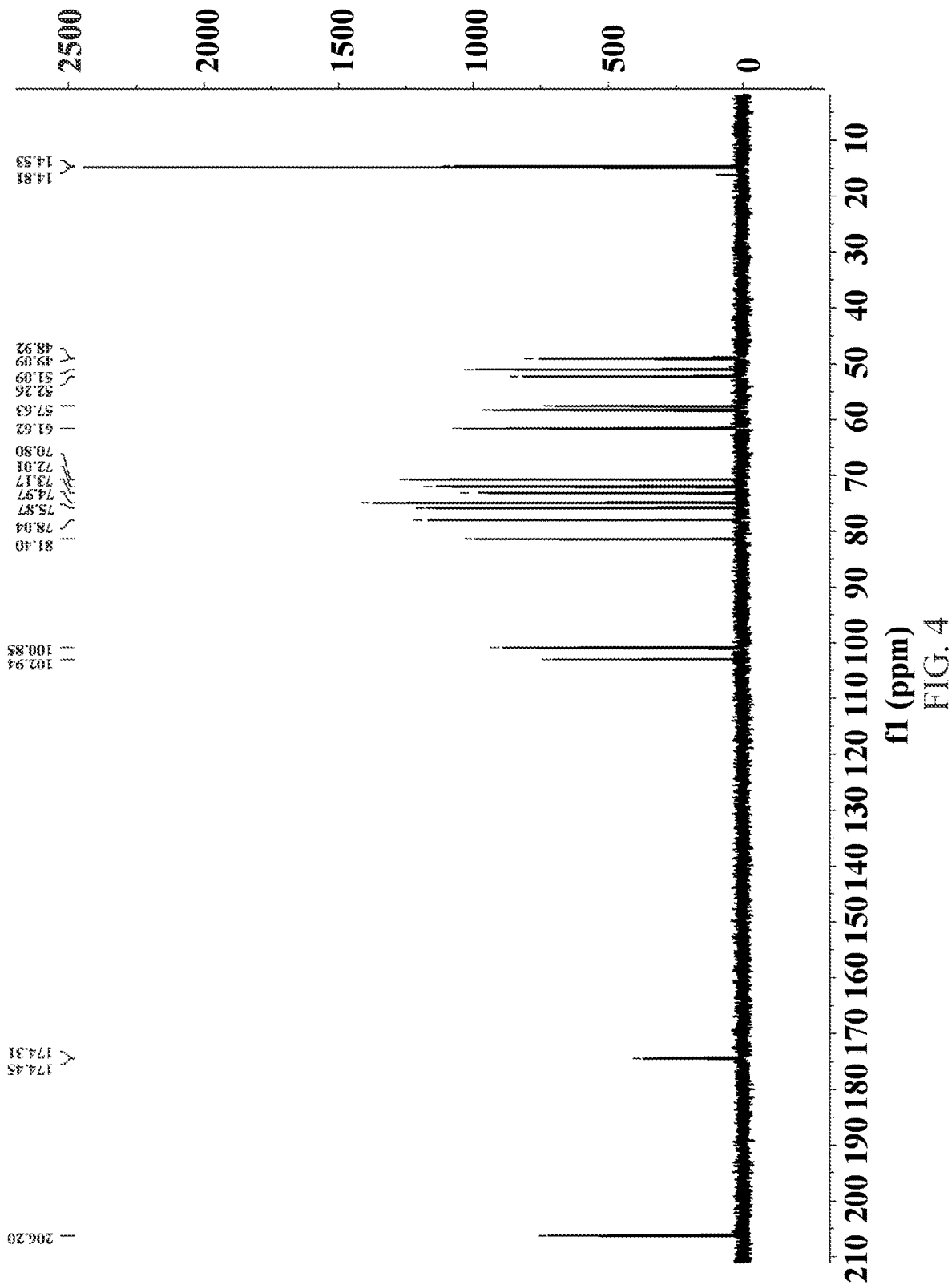
FIG. 4 is a carbon nuclear magnetic resonance spectrum of ARP prepared by an alanine/xylose reaction in Embodiment 1.

The obtained ARP solution was analyzed by a high performance liquid chromatography-evaporative light scattering detector (HPLC-ELSD), and separated and identified by an Amide chromatographic column (3.5 μm, 4.6 mm×150 mm, Waters, USA), to obtain a liquid chromatogram as FIG. 1. It can be seen from the figure that the retention time of the ARP prepared by the alanine/xylose reaction was 17 min. The converted product was subjected to preliminary structure identification by Matrix-Assisted Laser Desorption/Ionization Time of Flight Mass Spectrometry (MALDI-TOF-MS), and a total ion chromatogram and a total ion mass spectrum were obtained as FIGS. 2A and B. Identified by MS/MS, the molecular weight of the converted product was MW=221, so the converted product was preliminarily confirmed as the target ARP prepared by the alanine/xylose reaction, and the molecular formula was $C_8H_{15}NO_6$. After further qualitative analysis by nuclear magnetic resonance, the nuclear magnetic resonance spectrums were shown in FIG. 3 and FIG. 4. From the $^1$H spectrum (FIG. 3) and $^{13}$C spectrum (FIG. 4) of nuclear magnetic resonance, the product can be determined as ARP obtained by the reaction of alanine and xylose. By calculation, the yield of ARP can reach 94.8%.

Embodiment 2

(1) 8.26 kg of phenylalanine, 15.00 kg of xylose and 0.1 kg of EGCG were taken and dissolved by adding 500 kg of water, and a pH value of the mixed solution was adjusted to 8.0.

(2) The mixed solution was placed in a thermal reaction flask under normal pressure, and heated at a temperature of 90° C. in a water bath for 60 min to obtain a reaction solution.

(3) The reaction solution obtained in step (2) was transferred into a flask and subjected to a vacuum decompression dehydration reaction at a constant temperature of 90° C. for 20 min. Then, an ice bath was used to terminate the reaction to obtain a solid reactant, and the solid reactant was redissolved with water to obtain an ARP solution.

Figure 5:
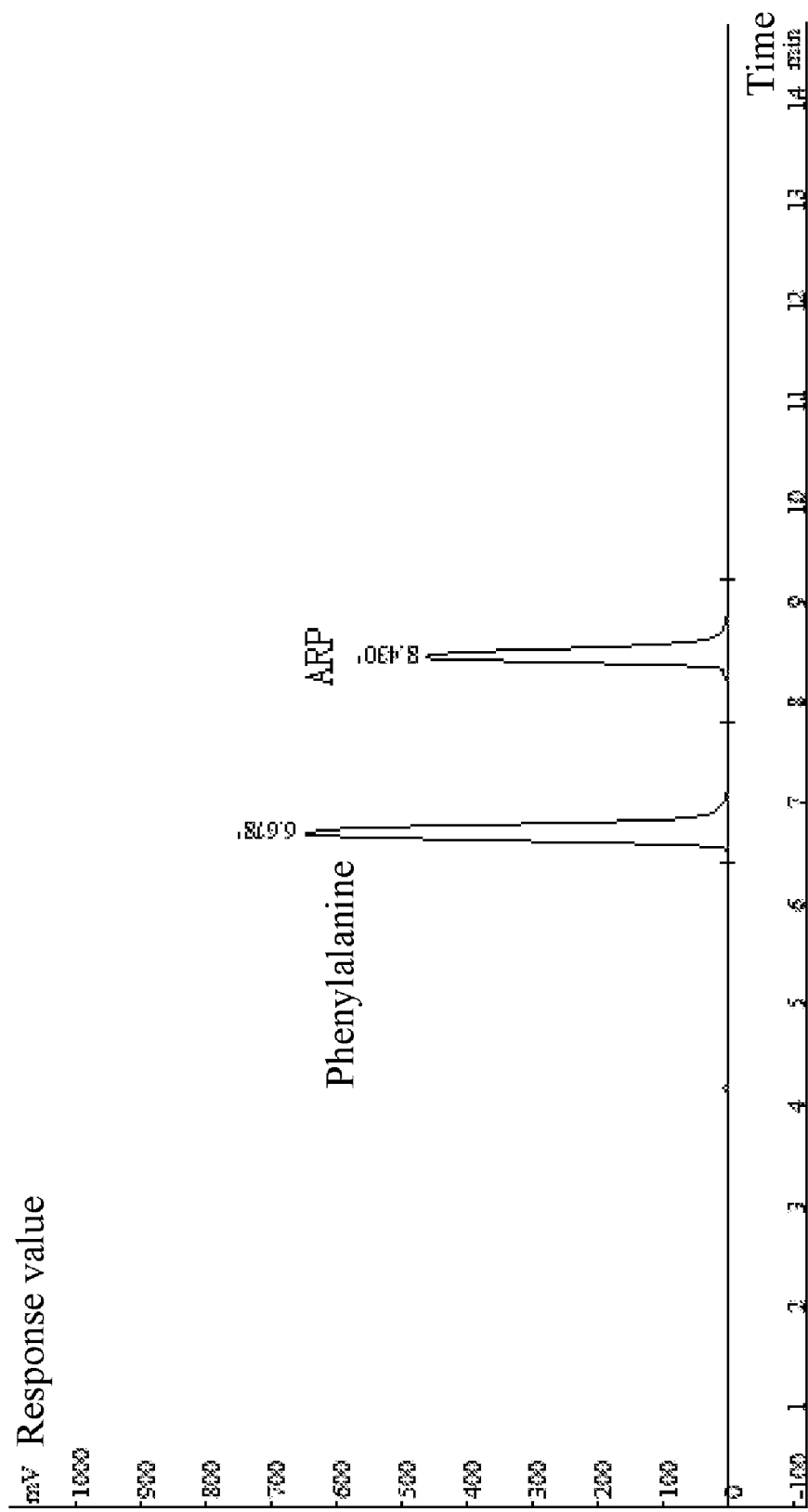
FIG. 5 is a chromatogram of an ARP solution prepared by a phenylalanine/xylose reaction in a water phase system added with EGCG in Embodiment 2.
Figure 6A:
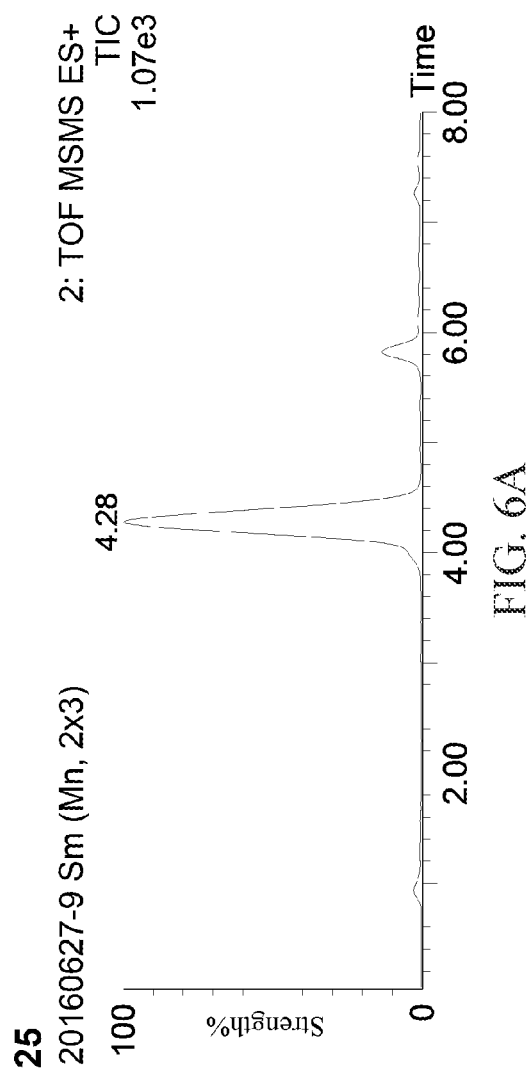
FIG. 6A shows a total ion chromatogram of ARP prepared by a purified phenylalanine/xylose reaction and qualitatively obtained by LC/MS/MS in Embodiment 2.
Figure 6B:
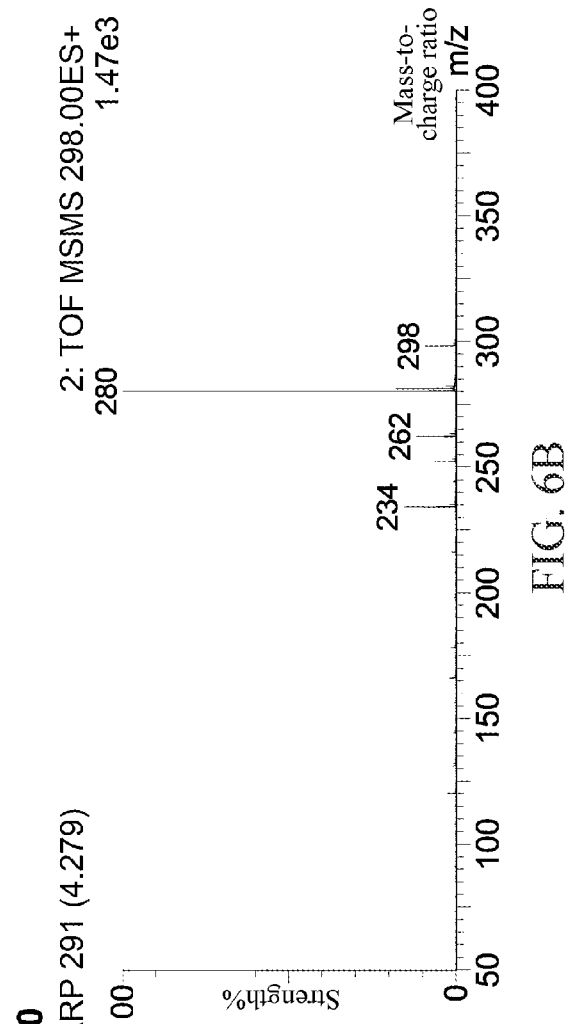
FIG. 6B shows a total ion mass spectrum of ARP prepared by a purified phenylalanine/xylose reaction and qualitatively obtained by LC/MS/MS in Embodiment 2.
Figure 7:
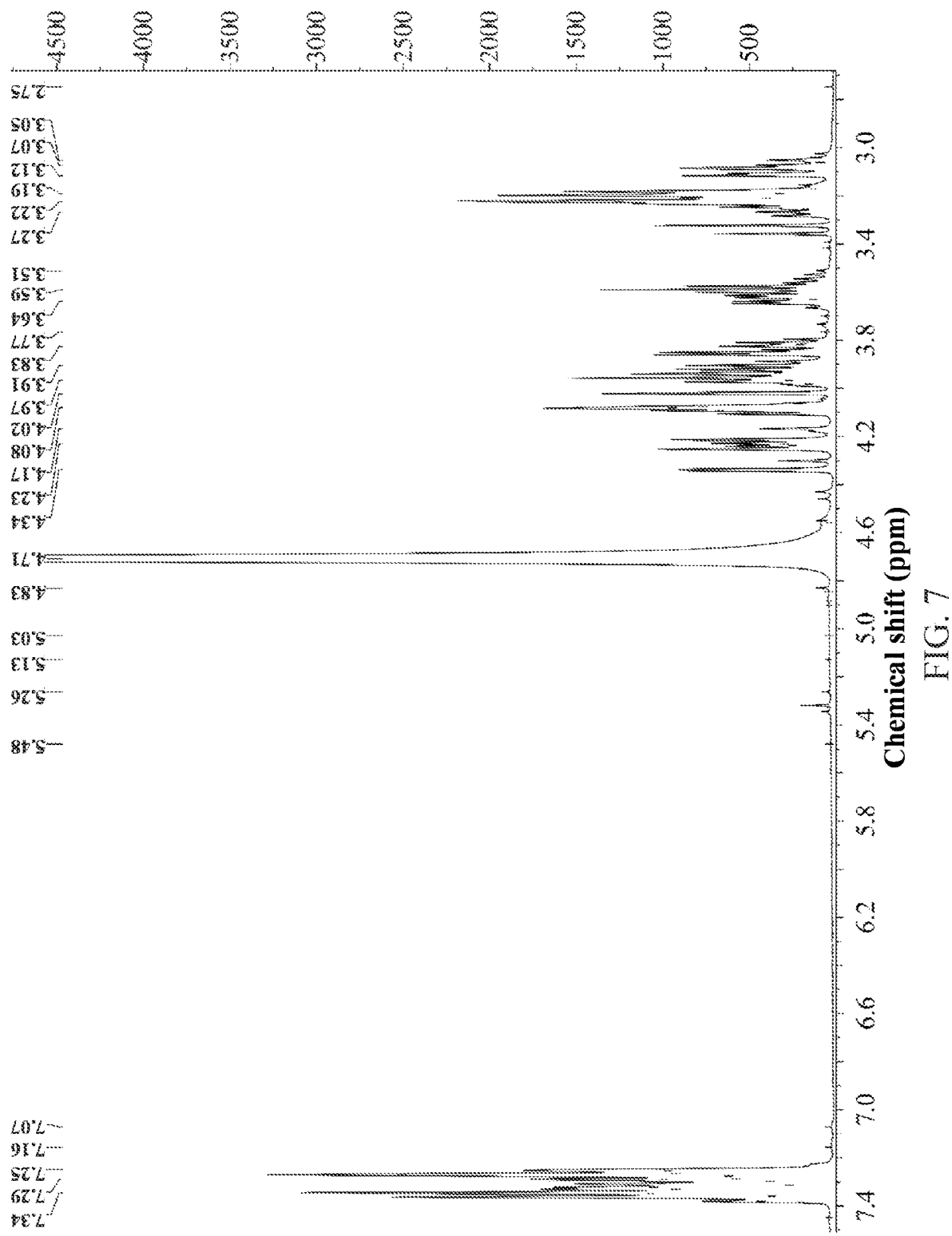
FIG. 7 is a hydrogen nuclear magnetic resonance spectrum of ARP prepared by a phenylalanine/xylose reaction in Embodiment 2.
Figure 8:
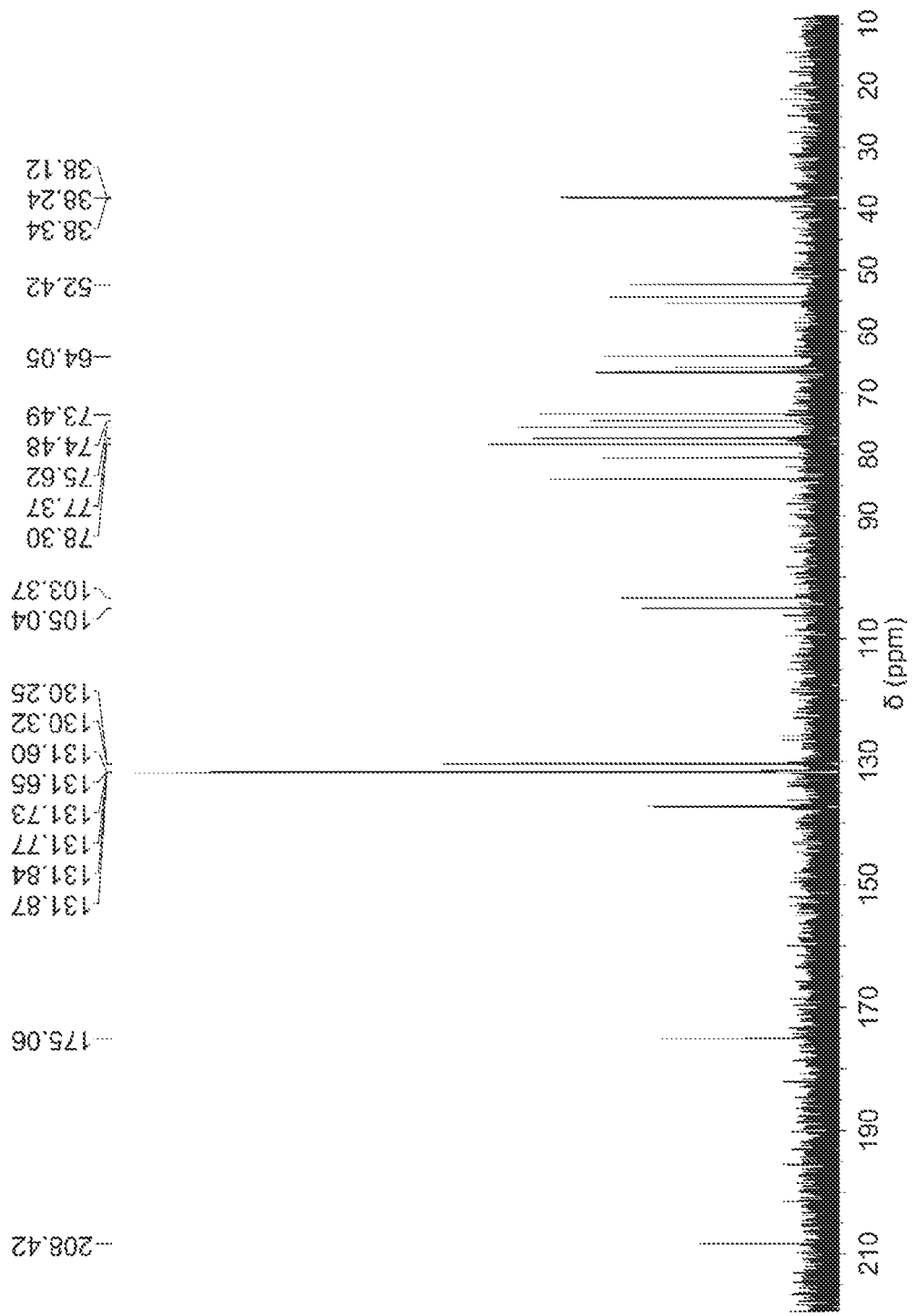
FIG. 8 is a carbon nuclear magnetic resonance spectrum of ARP prepared by a phenylalanine/xylose reaction in Embodiment 2.

The obtained ARP solution was analyzed by a high performance liquid chromatography-evaporative light scattering detector (HPLC-ELSD), and separated and identified by an Xselect CSH™ C18 chromatographic column (3.5 μm, 4.6 mm×150 mm, Waters, USA), so as to obtain a liquid chromatogram as FIG. 5. It can be seen from the figure that the retention time of the ARP prepared by phenylalanine/xylose was 8 min. The converted product was subjected to preliminary structure identification by Matrix-Assisted Laser Desorption/Ionization Time of Flight Mass Spectrometry (MALDI-TOF-MS), and a total ion chromatogram and a total ion mass spectrum were obtained as FIGS. 6A and 6B. Identified by MS/MS, the molecular weight of the converted product was MW=297, so the converted product was preliminarily confirmed as the target ARP prepared by the phenylalanine/xylose reaction, and the molecular formula was $C_{14}H_{19}NO_6$. After further qualitative analysis by nuclear magnetic resonance, the nuclear magnetic resonance spectrums were shown in FIG. 7 and FIG. 8. From the $^1$H spectrum (FIG. 7) and $^{13}$C spectrum (FIG. 8) of nuclear magnetic resonance, the product can be determined as ARP obtained by the reaction of phenylalanine and xylose. By calculation, the yield of phenylalanine/xylose ARP can reach 80.3%.

Embodiment 3

(1) 8.90 kg of alanine, 32.00 kg of xylose and 0.1 kg of EGCG were taken and dissolved by adding 500 kg of water, and a pH value of the mixed solution was adjusted to 7.5.

(2) The mixed solution was placed in a thermal reaction flask under normal pressure, and heated at a temperature of 90° C. in a water bath for 60 min to obtain a reaction solution.

(3) The reaction solution obtained in step (2) was transferred into a flask and subjected to a vacuum decompression dehydration reaction at a constant temperature of 90° C. for 10 min. Then, an ice bath was used to terminate the reaction to obtain a solid reactant, and the solid reactant was redissolved with water to obtain an ARP solution.

Figure 2B:
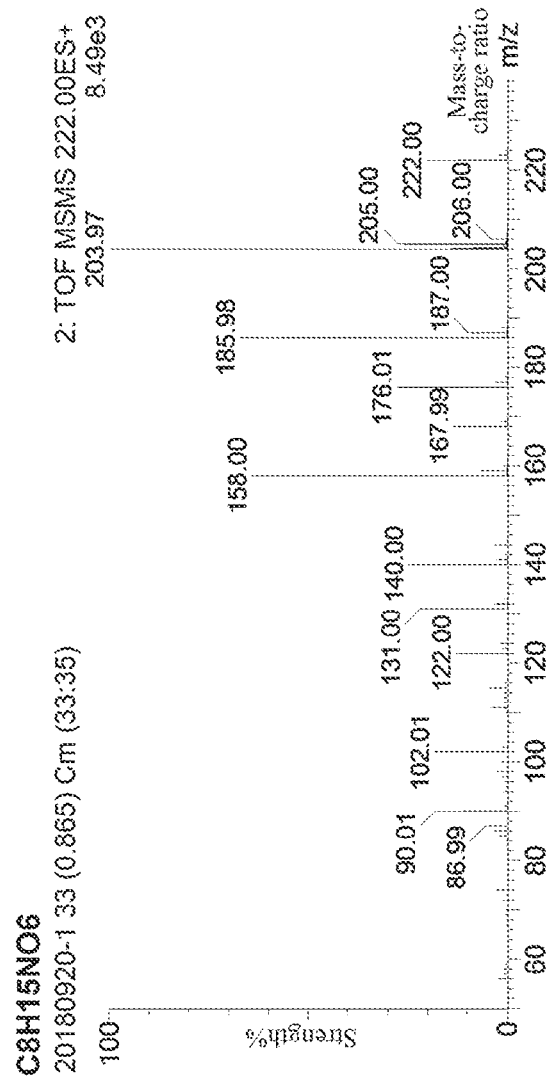
FIG. 2B shows a total ion mass spectrum of ARP prepared by a purified alanine/xylose reaction and qualitatively obtained by LC/MS/MS in Embodiment 1.
Figure 9:
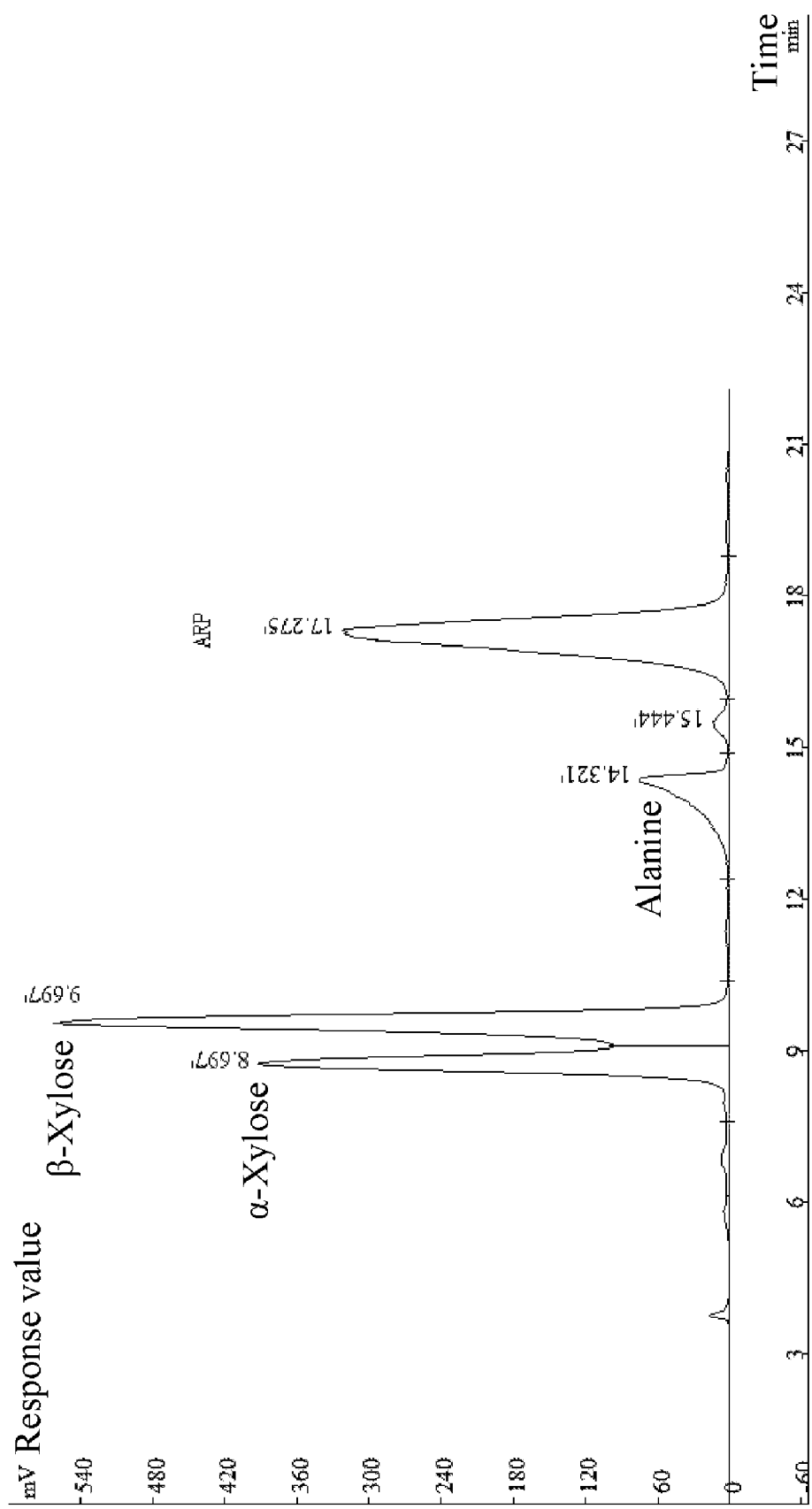
FIG. 9 is a chromatogram of an ARP solution prepared by an alanine/xylose reaction in a water phase system added with EGCG in Embodiment 3.

The obtained ARP solution was analyzed by a high performance liquid chromatography-evaporative light scattering detector (HPLC-ELSD), and separated and identified by an Amide chromatographic column (3.5 μm, 4.6 mm×150 mm, Waters, USA), so as to obtain a liquid chromatogram as FIG. 9. It can be seen from the figure that the retention time of the ARP prepared by the alanine/xylose reaction was 17 min. The converted product was subjected to preliminary structure identification by Matrix-Assisted Laser Desorption/Ionization Time of Flight Mass Spectrometry (MALDI-TOF-MS), and a total ion chromatogram and a total ion mass spectrum were obtained as FIGS. 2A and 2B. Identified by MS/MS, the molecular weight of the converted product was MW=221, so the converted product was preliminarily confirmed as the target ARP prepared by the alanine/xylose reaction, and the molecular formula was $C_8H_{15}NO_6$. After further qualitative analysis by nuclear magnetic resonance, the nuclear magnetic resonance spectrums were shown in FIG. 3 and FIG. 4. From the $^1H$ spectrum (FIG. 3) and $^{13}C$ spectrum (FIG. 4) of nuclear magnetic resonance, the product can be determined as ARP obtained by the reaction of alanine and xylose. By calculation, the yield of ARP can reach 85.6%.

Embodiment 4

(1) 10 kg of serine, 50 kg of ribose and 0.3 kg of catechin gallate (CG) were taken and dissolved by adding 900 kg of water, and a pH value of the mixed solution was adjusted to 6.0.

(2) The mixed solution was placed in a thermal reaction flask under normal pressure, and heated at a temperature of 60° C. in a water bath for 5 min to obtain a reaction solution.

(3) The reaction solution obtained in step (2) was transferred into a flask and subjected to a vacuum decompression dehydration reaction at a constant temperature of 60° C. for 60 min. Then, an ice bath was used to terminate the reaction to obtain a solid reactant, and the solid reactant was redissolved with water to obtain an ARP solution.

The obtained ARP solution was analyzed and calculated by high performance liquid chromatography, and the yield of ARP could reach 89.5%.

Embodiment 5

(1) 1 kg of methionine, 0.6 kg of arabinose and 0.05 kg of catechin gallate (CG) were taken and dissolved by adding 100 kg of water, and a pH value of the mixed solution was adjusted to 7.0.

(2) The mixed solution was placed in a thermal reaction flask under normal pressure, and heated at a temperature of 70° C. in a water bath for 60 min to obtain a reaction solution.

(3) The reaction solution obtained in step (2) was transferred into a flask and subjected to a vacuum decompression dehydration reaction at a constant temperature of 60° C. for 40 min. Then, an ice bath was used to terminate the reaction to obtain a solid reactant, and the solid reactant was redissolved with water to obtain an ARP solution.

The obtained ARP solution was analyzed and calculated by high performance liquid chromatography, and the yield of ARP could reach 83.5%.

COMPARATIVE EXAMPLE 1

(1) 8.90 kg of alanine and 32.00 kg of xylose were taken and dissolved by adding 500 kg of water, and a pH value of the mixed solution was adjusted to 7.5.

(2) The mixed solution was placed in a thermal reaction flask under normal pressure, and heated at a temperature of 90° C. in a water bath for 60 min to obtain a reaction solution.

Figure 10:
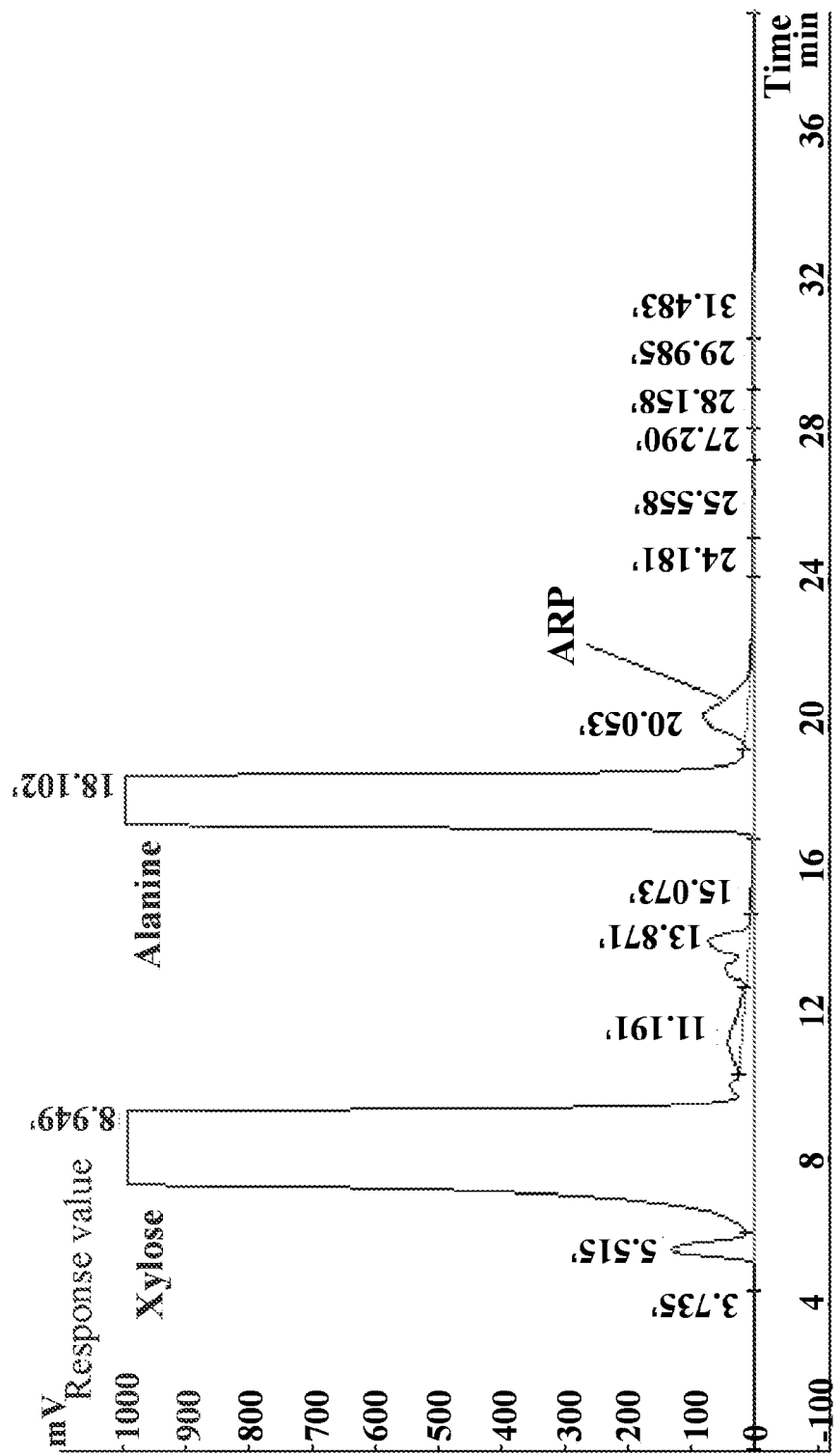
FIG. 10 is a chromatogram of an ARP solution prepared by an alanine/xylose reaction in an atmospheric water phase system without EGCG addition in Comparative Example 1.

The reaction solution was analyzed by high performance liquid chromatography, and the result is shown in FIG. 10. It can be seen from FIG. 10 that the retention time of the ARP prepared by the alanine/xylose reaction in the present comparative example was 20 min, and the yield was 2.2%.

COMPARATIVE EXAMPLE 2

(1) 8.90 kg of alanine and 32.00 kg of xylose were taken and dissolved by adding 500 kg of water, and a pH value of the mixed solution was adjusted to 7.5.

(2) The mixed solution was placed in a thermal reaction flask under normal pressure, and heated at a temperature of 90° C. in a water bath for 60 min to obtain a reaction solution.

(3) The reaction solution obtained in step (2) was transferred into a flask and subjected to a vacuum decompression dehydration reaction at a constant temperature of 90° C. for 10 min. Then, an ice bath was used to terminate the reaction to obtain a solid reactant, and the solid reactant was redissolved with water to obtain an ARP solution.

Figure 11:
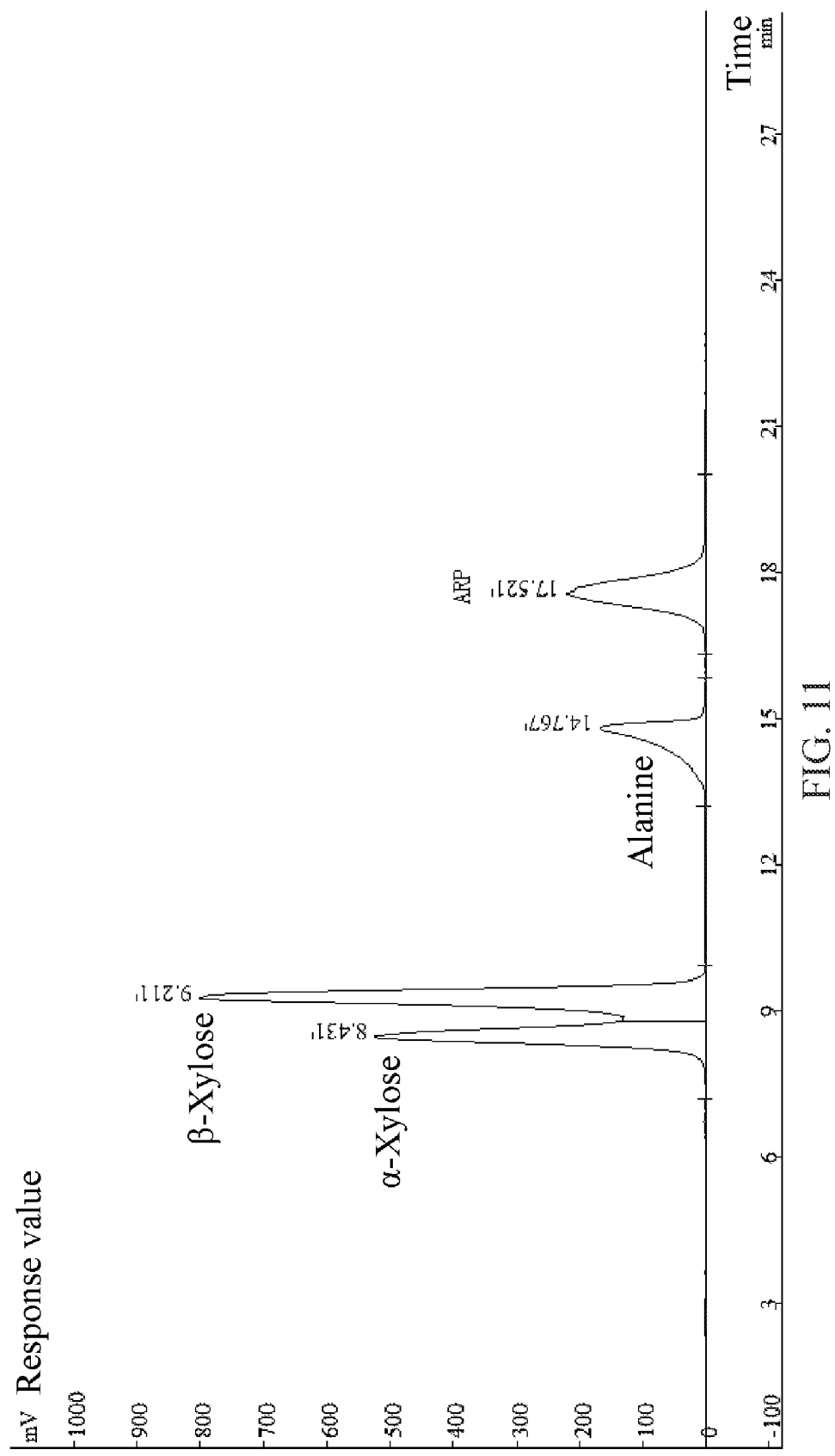
FIG. 11 is a chromatogram of an ARP solution prepared by an alanine/xylose reaction in a vacuum decompression water phase system without EGCG addition in Comparative Example 2.

The obtained ARP solution was analyzed by high performance liquid chromatography, and the result is shown in FIG. 11. It can be seen from FIG. 11 that in the alanine/xylose system without EGCG addition, the retention time of the ARP prepared by the alanine/xylose reaction was 17 min, and the yield of ARP was 42.1%, which was much higher than the yield of 2.2% in the atmospheric water phase reaction in Comparative Example 1. It shows that in the absence of tea polyphenols, that is, under the condition of no deoxyosone trap effect, pure vacuum decompression dehydration has a certain promoting effect on the formation of ARP. The result confirms the importance of decompression vacuum dehydration in the technology disclosed in the present invention. The ARP yield (94.8%) obtained in Embodiment 1, compared with Comparative Example 1, was increased by 43 times; and compared with Comparative Example 2, was increased by 225.2%. The importance of the tea polyphenols in the preparation process of the ARP in a water phase in the present invention is confirmed, and the technological progress of the present invention is reflected.

COMPARATIVE EXAMPLE 3

Figure 12:
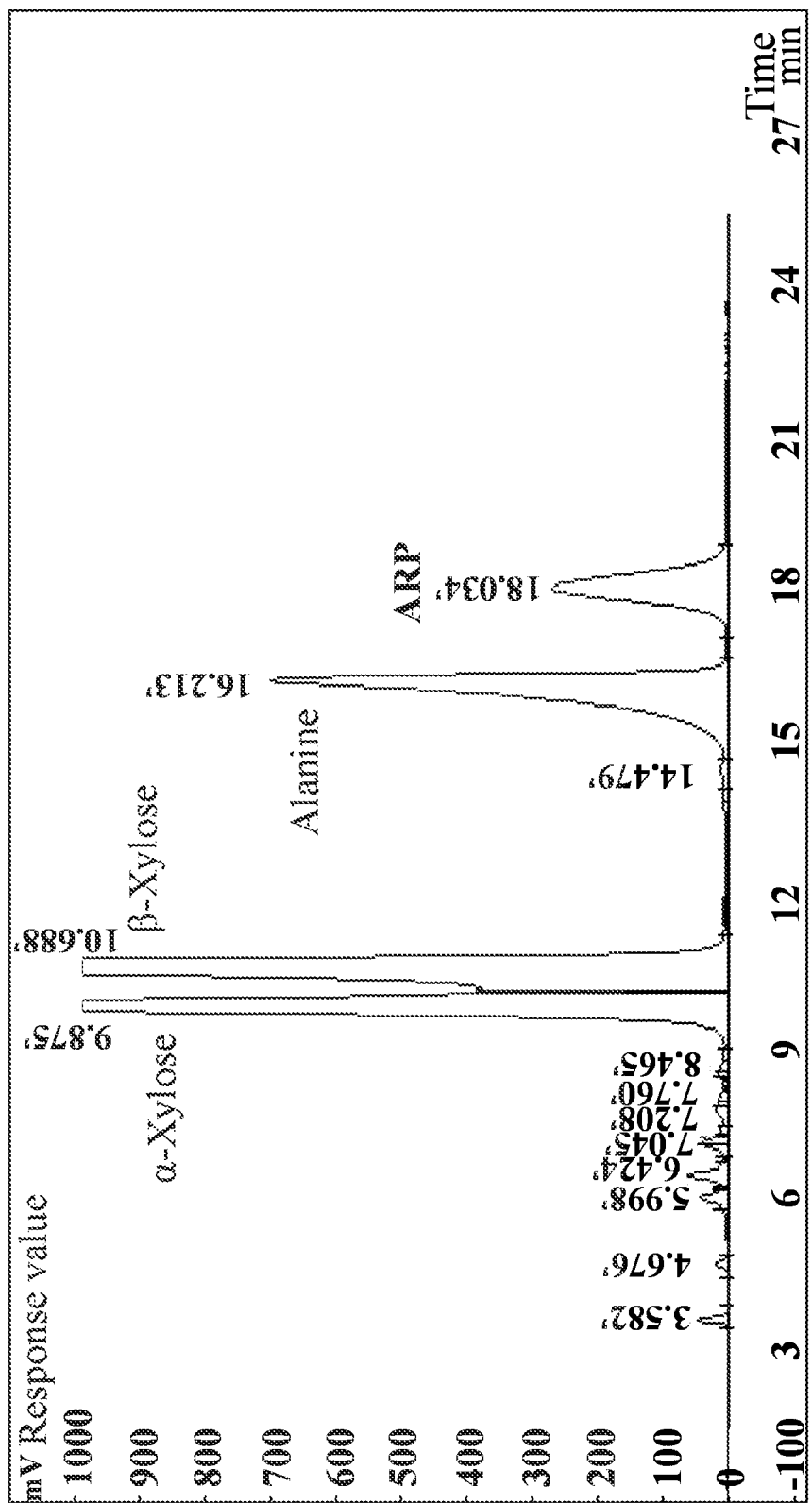
FIG. 12 is a chromatogram of an ARP solution prepared by an alanine/xylose reaction in an absolute methanol system in Comparative Example 3.

8.90 kg of alanine and 32.00 kg of xylose were taken and dissolved by adding 500 kg of absolute methanol. After heating under reflux at a temperature of 60° C. in a water bath for 6 hours, the reaction solution was taken and analyzed by high performance liquid chromatography. The analysis method was the same as that in Embodiment 1, a chromatogram of the alanine/xylose ARP prepared in an organic phase was obtained, and the result is shown in FIG. 12. In the present comparative example, the retention time of the ARP prepared by the alanine/xylose reaction was 18 min, and the ARP yield was 35.8%. It can be seen from the chromatogram 12 that the ARP prepared in the organic reagent absolute methanol has more impurity peaks, which proves that the reaction system has more byproducts. Compared with the present comparative example, the ARP yield (94.8%) prepared in a water phase of the alanine/xylose system added with EGCG in Embodiment 1 is increased by 264.8%. It is confirmed that the technical method of the present invention can significantly increase the ARP yield compared with a traditional organic reagent method, and the technological progress of the present invention is reflected.

COMPARATIVE EXAMPLE 4

(1) 8.26 kg of phenylalanine and 15.00 kg of xylose were taken and dissolved by adding 500 kg of water, and a pH value of the mixed solution was adjusted to 8.0.

(2) The mixed solution was placed in a thermal reaction flask under normal pressure, and heated at a temperature of 90° C. in a water bath for 60 min to obtain a reaction solution.

(3) The reaction solution obtained in step (2) was transferred into a flask and subjected to a vacuum decompression dehydration reaction at a constant temperature of 90° C. for 20 min. Then, an ice bath was used to terminate the reaction to obtain a solid reactant, and the solid reactant was redissolved with water to obtain an ARP solution.

Figure 13:
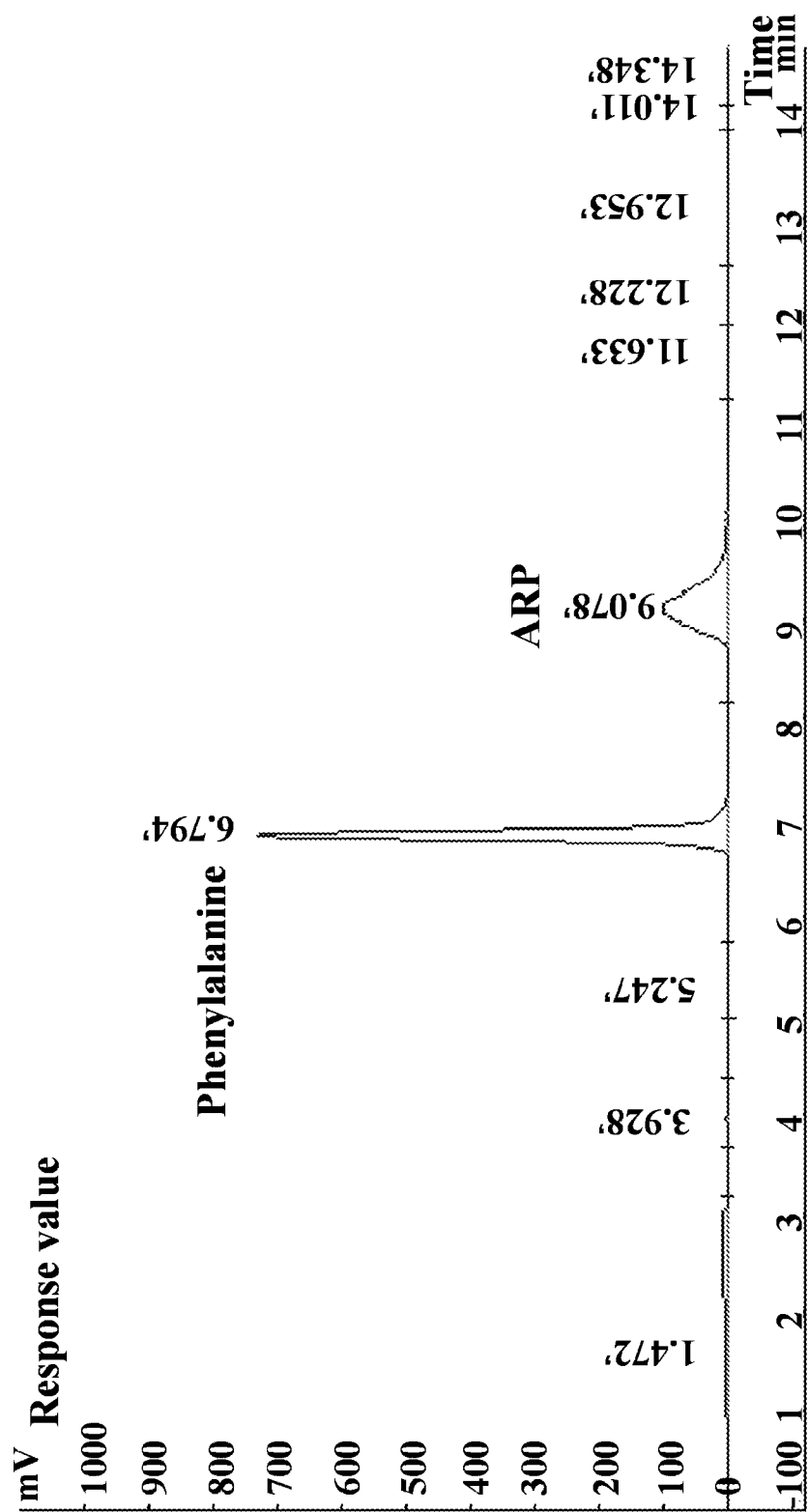
FIG. 13 is a chromatogram of an ARP solution prepared by a phenylalanine/xylose reaction in a water phase system without EGCG addition in Comparative Example 4.
Figure 14A:
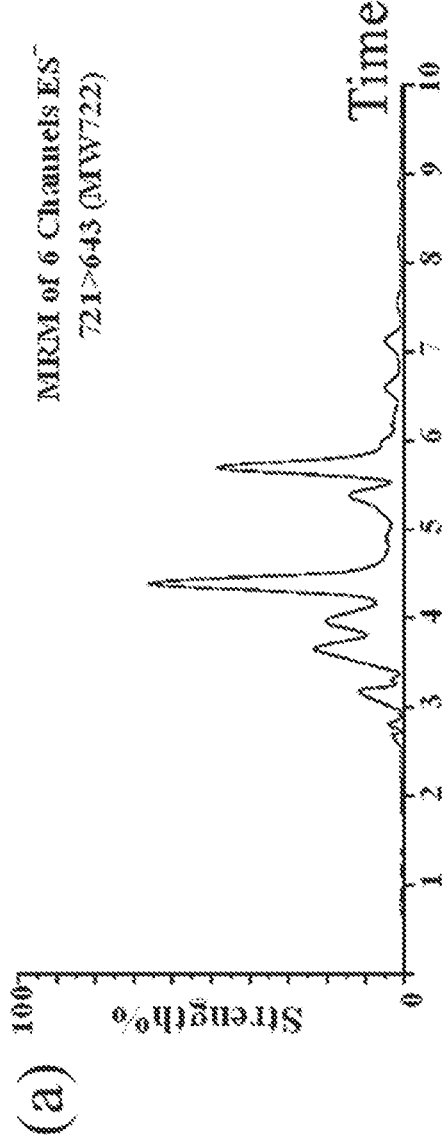
FIGS. 14A-F show the total ion chromatograms of adducts of tea polyphenol, ARPT and degradation products DP thereof.
Figure 14B:
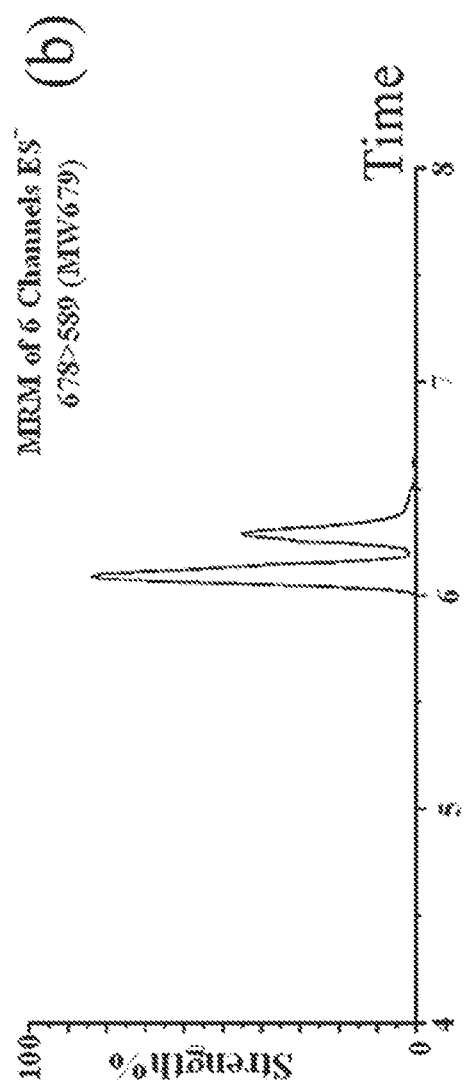
Figure 14C:
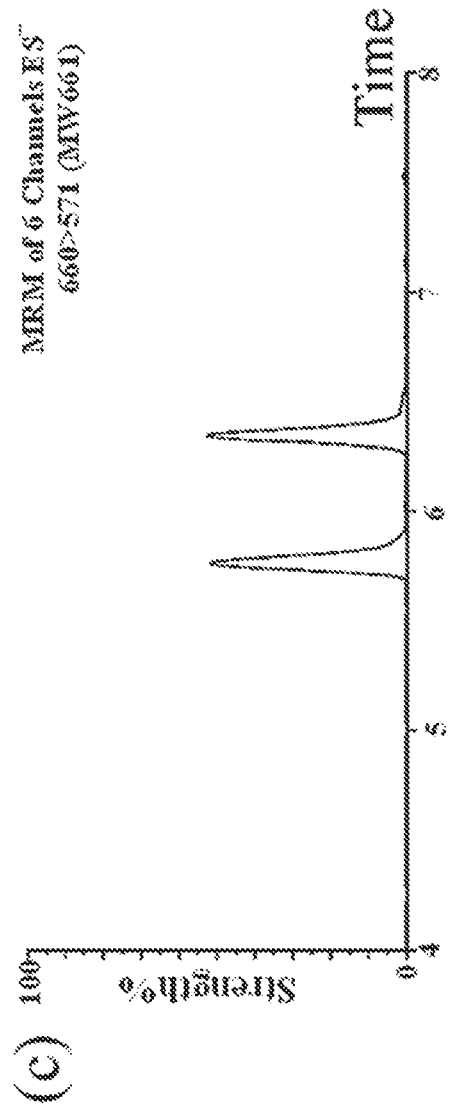
Figure 14D:
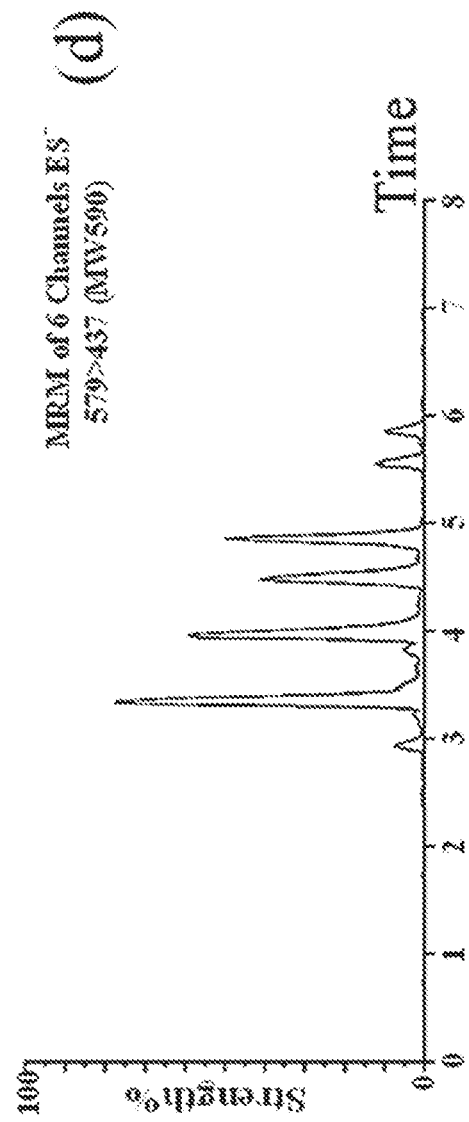
Figure 14E:
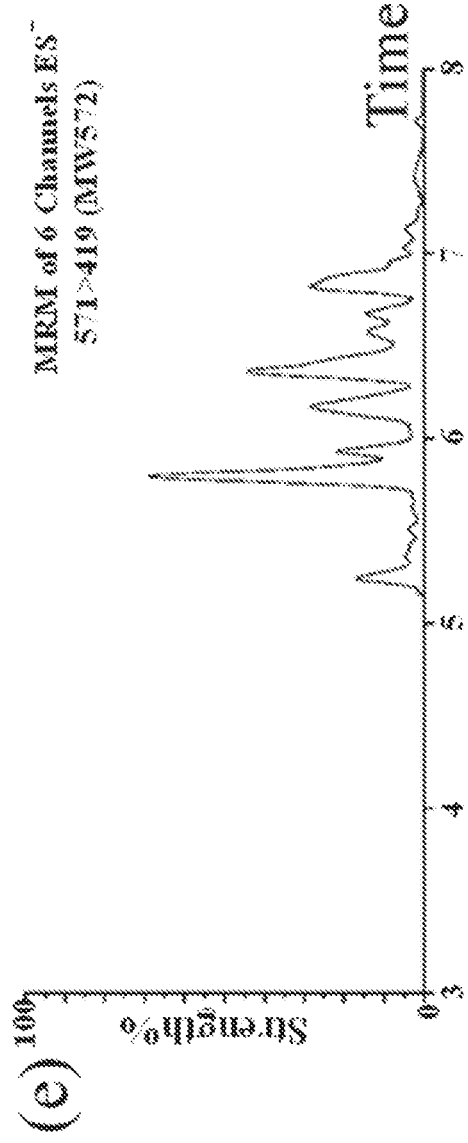
Figure 14F:
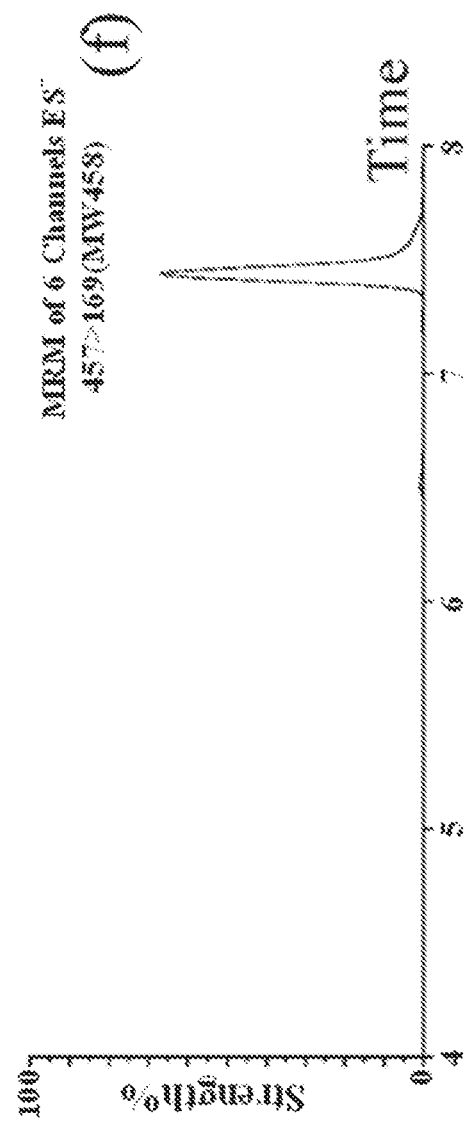
Figure 15:
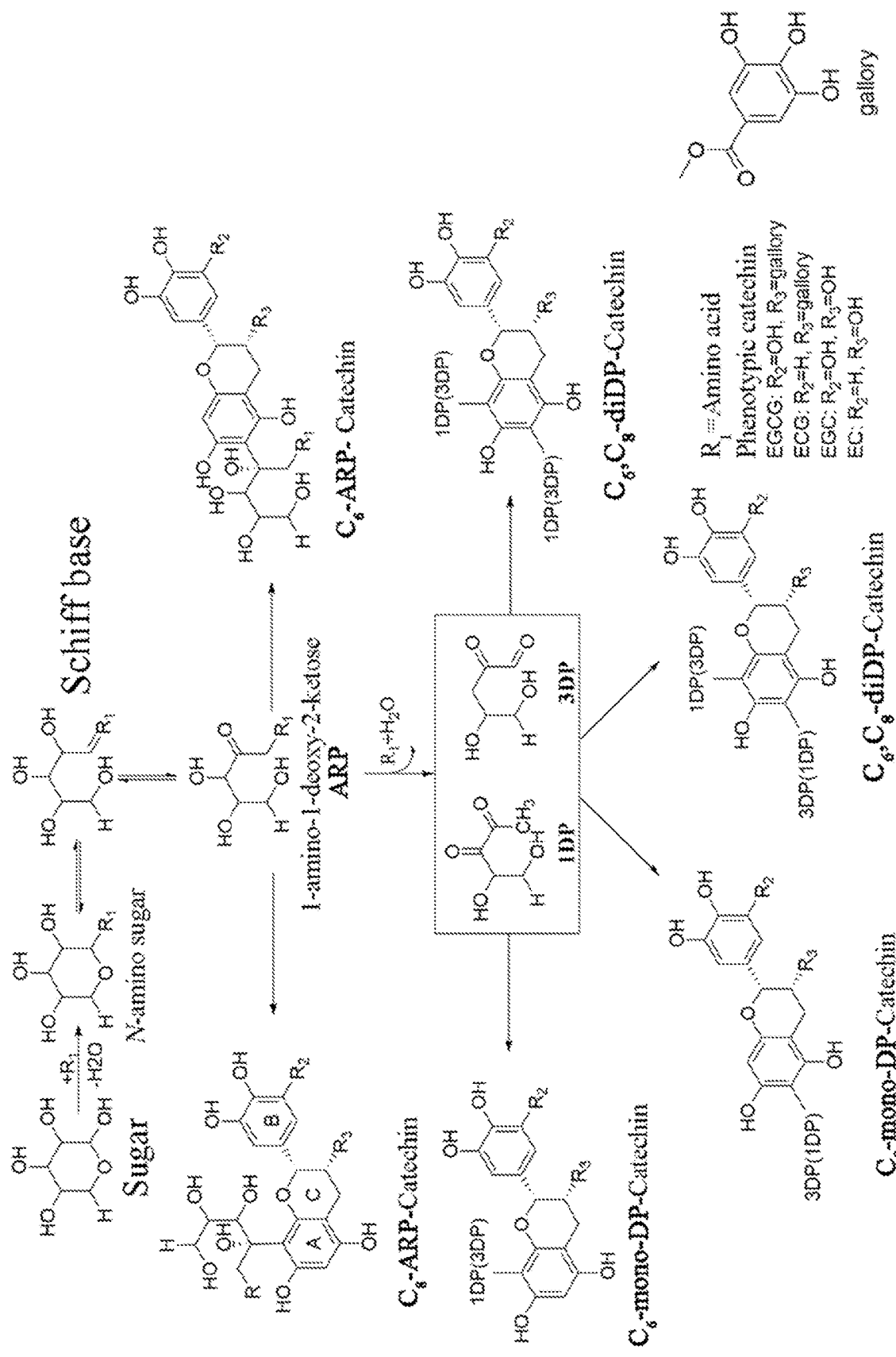
FIG. 15 shows a trap effect mechanism of tea polyphenols on ARP degradation products.
Figure 16:
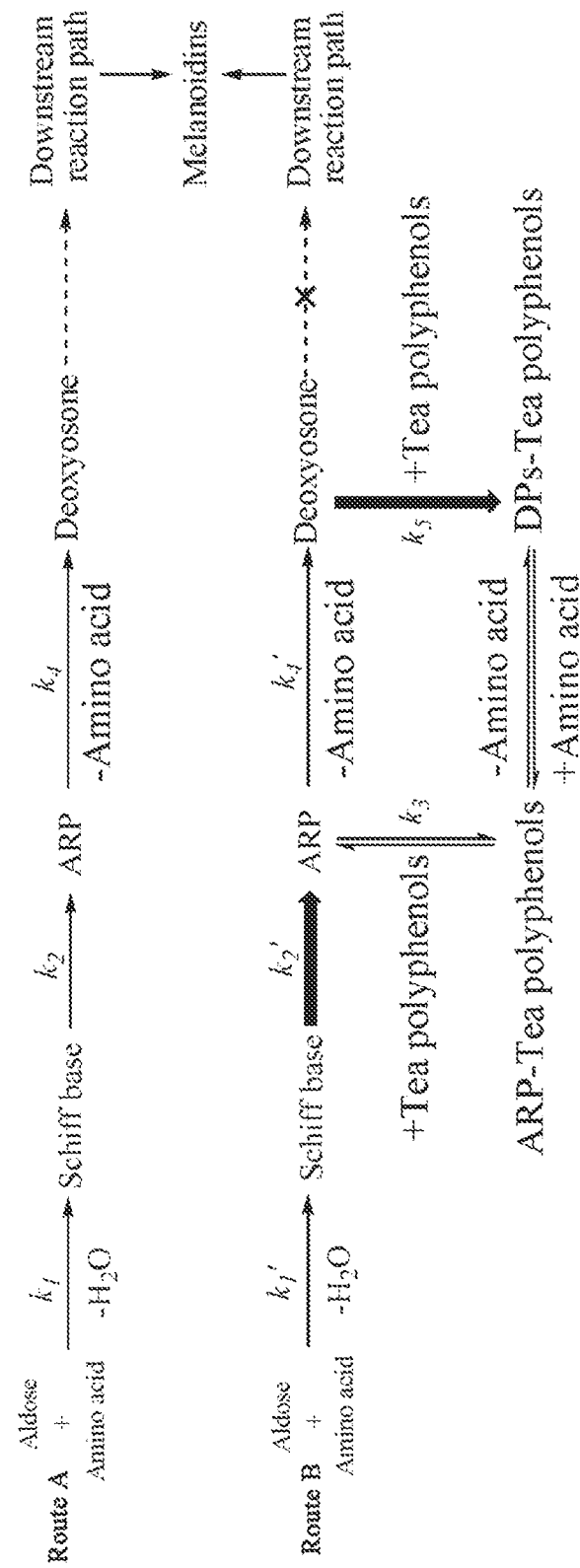
FIG. 16 shows a kinetic mechanism that tea polyphenols promote formation of ARP and inhibit degradation of ARP.

The ARP solution was analyzed by high performance liquid chromatography, and the result is shown in FIG. 13. It can be seen from FIG. 13 that in the phenylalanine/xylose system without EGCG addition, the phenylalanine/xylose ARP retention time was 9 min, and the yield of ARP was 35.6%. Compared with the present comparative example, the ARP yield (82.3%) of the phenylalanine/xylose system added with EGCG in Embodiment 2 is increased by 231.2%. The importance of the tea polyphenols in the preparation process of ARP in a water phase in the present invention is confirmed, and the technological progress of the present invention is reflected.

The experimental water in the above embodiments and comparative examples is distilled water, the sugars and amino acids are all food grade, the chemical reagents used in the high performance liquid chromatography analysis experiment are chromatographically pure, and the rest chemical reagents are analytically pure. The detection conditions of high performance liquid chromatography are as follows: the mobile phase is acetonitrile and water, the flow rate is 0.6 mL/min, gradient elution is used, and the column temperature is 35° C. The conditions of mass spectrometry analysis are as follows: an ESI+ mode is used, the detector voltage is 1.8 kV, the capillary voltage is 3.5 kV, the cone voltage is 20 V, and the extraction voltage is 7 V. The electron source temperature and the desolvation gas temperature are 100° C. and 400° C., respectively, the gas flow rate is 700 L/h, and the cone gas flow rate is 50 L/h. A sample is scanned in a range of m/z 20 to 1000 mass-to-charge ratio, the scanning time is 1 s, and the scanning time delay is 0.1 s. The separated pure intermediate is dissolved in $D_2O$, the intermediate is analyzed with a nuclear magnetic resonance instrument, and the test temperature is 298 K.

The above are only preferred embodiments of the present invention, and are not intended to limit the present invention. Any modification, equivalent replacement, improvement and the like made without departing from the spirit and principle of the present invention should fall within the scope of the present invention.

What is claimed is:

1. A method for increasing a yield of Amadori rearrangement products (ARP), wherein the method is based on a mechanism of inhibiting a degradation of the Amadori rearrangement products by adding tea polyphenols to deoxyosones, and the method comprises the following steps:
   (1) dissolving and mixing amino acid, sugar, and the tea polyphenols in water to obtain a mixed solution, and adjusting a pH value of the mixed solution;
   (2) placing the mixed solution obtained in step (1) in a reaction flask, and heating the reaction flask at a constant temperature in a water bath to obtain a reaction solution; and
   (3) performing a vacuum decompression dehydration reaction on the reaction solution obtained in step (2) at a constant reaction temperature; after the vacuum decompression dehydration reaction is completed, using an ice bath to terminate the vacuum decompression dehydration reaction to obtain a solid reactant; and redissolving the solid reactant in water to obtain an ARP solution, wherein in step (3), an ARP yield in the ARP solution is 80% or above.

2. The method according to claim 1, wherein the tea polyphenols in step (1) comprise at least one selected from the group consisting of epicatechin, epigallocatechin, epicatechin gallate, epigallocatechin gallate, catechin, gallocatechin, catechin gallate and gallocatechin gallate.

3. The method according to claim 1, wherein the amino acid in step (1) is at least one selected from the group consisting of alanine, phenylalanine, serine and methionine.

4. The method according to claim 1, wherein the sugar in step (1) is at least one selected from the group consisting of ribose, xylose, arabinose and glucose.

5. The method according to claim 1, wherein dosages by mass of the amino acid, the sugar and the tea polyphenols in step (1) are: 10 parts of the amino acid, 5-50 parts of the sugar, 0.1-5 parts of the tea polyphenols, and 200-1200 parts of the water.

6. The method according to claim 1, wherein in step (1), the pH value of the mixed solution is 6-9.

7. The method according to claim 1, wherein in step (2), the constant temperature of the water bath is 60-90° C., and a heating time is 30-100 min.

8. The method according to claim 1, wherein in step (3), the constant reaction temperature is 60-90° C., and a reaction time is 5-60 min; and a temperature of the ice bath is 0° C.

* * * * *